United States Patent [19]
Wagner

[11] Patent Number: 5,770,153
[45] Date of Patent: Jun. 23, 1998

[54] INTEGRATED ANALYTICAL DEVICE FOR DETERMINING THE GAS CONSUMPTION OF MATTER

[75] Inventor: Ingeborg Wagner, Gmund, Germany

[73] Assignee: WTW Wissenschaftlich-Technische Werkstatten GmbH, Weilheim, Germany

[21] Appl. No.: 505,034

[22] Filed: Jul. 21, 1995

[51] Int. Cl.[6] .................................................... G01N 7/00
[52] U.S. Cl. ................... 422/79; 435/287.5; 435/288.1; 436/62; 436/148
[58] Field of Search ......................... 422/79, 80; 436/62, 436/148; 435/287.5, 288.1

[56] References Cited

U.S. PATENT DOCUMENTS

| | | | |
|---|---|---|---|
| 3,907,646 | 9/1975 | Wilkins et al. | 435/287.5 |
| 3,915,636 | 10/1975 | Ford, Jr. et al. | 436/148 |
| 4,829,809 | 5/1989 | Tantram et al. | 422/80 |
| 5,232,839 | 8/1993 | Eden et al. | 435/287.5 |
| 5,281,395 | 1/1994 | Markart et al. | 422/67 |

OTHER PUBLICATIONS

Atkinson et al. Biochemical Engineering and Biotechnology Handbook, The Nature Press (1983) pp. 114–153.

*Primary Examiner*—Jan Ludlow
*Attorney, Agent, or Firm*—Smith-Hill and Bedell

[57] ABSTRACT

An analytical device for determining the gas consumption of matter, specifically the oxygen demand of organic matter includes a container for holding the sample which is to be analyzed and a cop to seal the container gas-tight. Electrical and/or electronic measurement components are integrated in the cap. These components include an electrical pressure sensor which communicates with the interior of the container through a pressure connection, electronic measuring circuitry to which the pressure sensor output signal is sent in order to calculate a value which is proportional to gas consumption, keys for operating the electronic measuring circuitry, and a display for displaying measured, calculated, or stored values. The cap also contains a power source for the electrical/electronic components.

18 Claims, 3 Drawing Sheets

INTEGRATED ANALYTICAL DEVICE FOR DETERMINING THE GAS CONSUMPTION OF MATTER

BACKGROUND OF THE INVENTION

The invention relates to an analytical device for determining the gas demand, in particular the oxygen demand, of matter, in particular organic matter.

Such analytical devices are primarily used to analyze waste water to determine the oxygen demand of the organic cells contained in the water. This measurement is also referred to as a BOD measurement (Biological Oxygen Demand). To date, such analytical devices have consisted of a container onto which a cap is screwed to form a gas-tight seal. A pressure line extends from the cap to a mercury manometer, which displays the pressure continuously. This device is generally placed in a climatically controlled chamber in order to obtain a uniform reference temperature, thus simplifying the calculation of the biological oxygen demand based on the pressures displayed by the mercury manometer. As a rule, such an analytical device comprises a plurality of containers located on magnetic stirrer platforms, so that a number of samples can be analyzed simultaneously. However, use of mercury manometers is increasingly coming into disfavor given the hazards associated with working with this highly toxic metal. Furthermore, it is very difficult to read the pressures from the manometers, especially if the device is located near the bottom of a climatic chamber.

Thus, the object of the invention is to provide an analytical device which is environmentally sound, easy to read, and easy to handle. Additionally, the device should not be sensitive to soiling and contamination.

This object is met by an analytical device in accordance with the invention.

SUMMARY OF THE INVENTION

In the invention, a pressure measurement is performed by means of an electrical or electronic sensor. The sensor, together with the entire electronic measuring circuitry including the display, is integrated in the cap of the test container. Thus, the following components are integrated in the cap: an electrical pressure sensor, which communicates with the pressure on the interior of the container, electronic measuring circuitry to which the output signal from the pressure sensor is sent in order to calculate a value which is proportional to gas demand, a set of keys to operate the electronic measuring circuitry, a display to indicate measured, calculated, or stored values, and a power source for the components, preferably a battery. These components are placed in the cap in such a way that they are protected from contamination and moisture entry by the outer contour of the cap. The display is produced, for example, by means of an LCD or LED display. The pressure sensor may either be open toward and facing the interior of the container, or it may be separated from the interior of the container by a gas-permeable waterproof membrane, for example a PTFE membrane. In this way, contamination of the pressure sensor, which would occur for example if the container were to tip or if a great deal of foam were produced, can be avoided.

The advantages of the invention are obvious. An extremely compact analytical device is produced. It can be manufactured economically, and the amount of gas consumed by matter, in particular the biological oxygen demand (BOD), can be determined with a minimum outlay for equipment. Mercury manometers are no longer necessary, which means that the device can operate without employing toxic substances.

The container may be embodied as a bottle. The cap has a threaded part that fits to the neck of the bottle and the measuring circuitry and associated components are located in an enlarged spherical or elliptical part of the cap. The enlarged part of the cap should not extend beyond the outside contour of the bottle. In this way, the bottles can be arranged as close to one another as possible without causing the analytical devices mounted on the bottle tops to interfere with one another.

Preferably, the analytical device can possess a fill level sensor, which permits the volume of test substance in the container to be measured automatically. A fill level sensor can operate based on electrical, optical, or ultrasonic principles. Since the container volume is a specified constant value, the gas consumption (gas demand) can be calculated directly and be shown on the display. In this case, a manual re-calculation is no longer necessary.

The device can also contain a temperature sensor to compensate for temperature or the effect of temperature changes on the measured value.

The device has a memory in which either a permanently entered reference value or the most recently outputted test value can be stored, so that if a new measurement is made, the new calculated value can be compared against the reference value or against the most recently recalled test value.

If an internal clock is provided inside the analytical device, the changes in the values over time can be taken into account automatically by the electronic measuring circuitry.

Thus, the memory areas in the electronic measuring circuitry can be configured to store parameters such as the container volume, contents volume, temperature, pressure, and time as well as to store measured or reference values.

If the device has a data exchange interface, in particular a contactless interface, the measured and/or stored values can be loaded into a larger processor for measurement data evaluation and presentation.

As already indicated, the cap used to hold the device consists of an enlarged part above the threaded part of the cap. The enlarged part may assume the shape of a sphere which is compressed along the vertical axis. The cap then preferably comprises two hemispherical shells which are screwed together along a horizontal plane. The space for a battery or an accumulator is provided in the vicinity of the sides of the half shells which are facing one another. The joint between the two half shells can be protected from moisture intrusion by means of an o-ring seal.

The LCD or LED display is preferably arranged in the cap in such a way that the display extends flush to the outer contour of the cap, either of its own accord or by means of a transparent display window. This greatly reduces the susceptibility to contamination and soiling.

The set of keys used to operate the electronic measuring circuitry should be provided in the form of momentary-contact switches which preferably are hermetically sealed as in a film keypad. In this way, moisture cannot enter the device, either in the area of the display or in that of the keys. Thus, the device can even be washed off, which makes is particularly well suited for waste water analysis.

Since the container generally assumes the shape of a bottle, it is advantageous if the cap, which can be screwed onto the bottle, is also hemispherical, so that it is constructed in an ergonomic design to facilitate screwing the cap onto and off the bottle.

In an embodiment of the invention which can be used for various measurements, an electromagnetically operated valve can be located in the cap. This valve can be actuated by the electronic measuring circuitry based on a calculated value or on a time in order to allow the interior of the container to communicate with the outside atmosphere or with a connection to the exterior located on the cap. In this way, the pressure on the inside of the container can be equalized in a controlled manner with the ambient air or with a reference atmosphere.

BRIEF DESCRIPTION OF THE DRAWINGS

The invention is described below in the form of a typical embodiment based on the schematic diagrams. These diagrams show.

DETAILED DESCRIPTION

Figure 1:
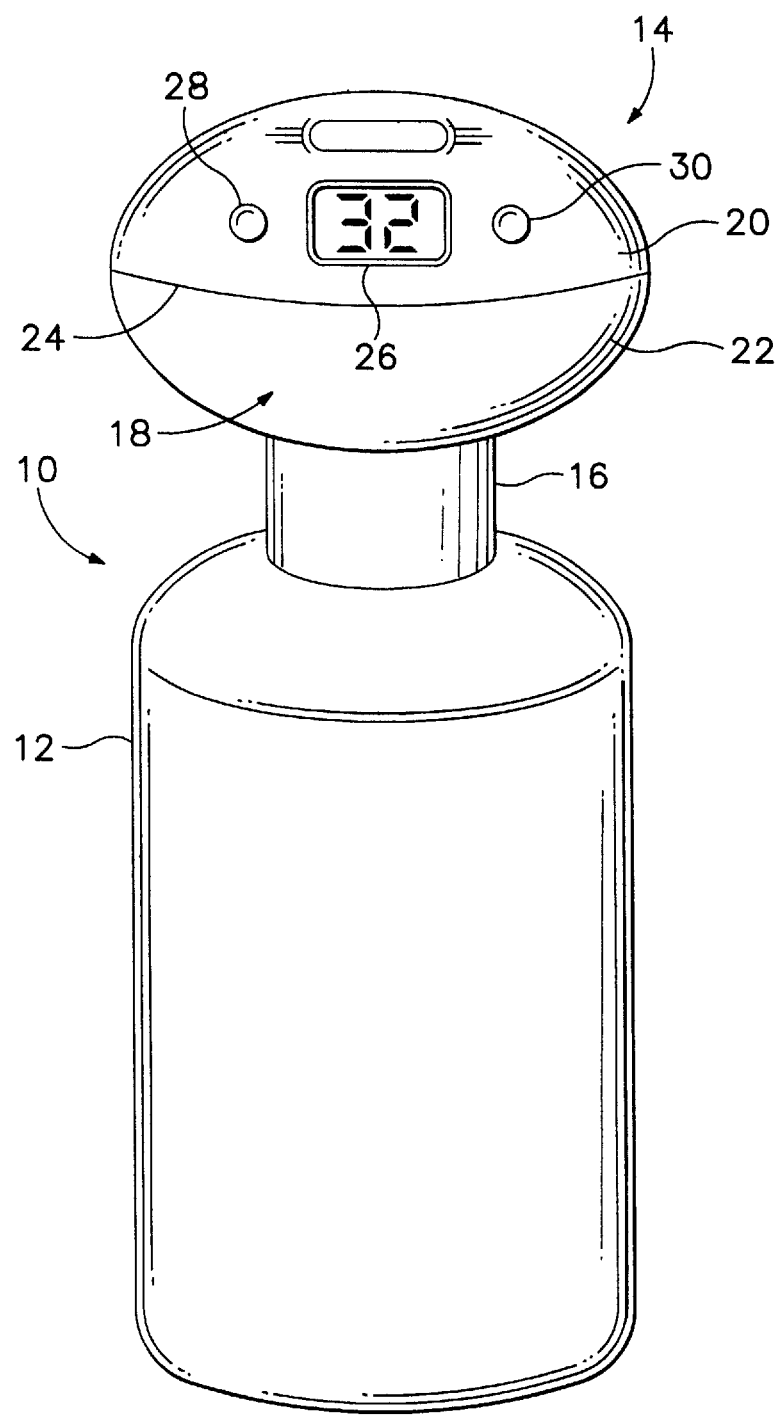
FIG. 1 is a perspective view of an analytical device consisting of the bottle and the screw-on measurement head.
Figure 2:
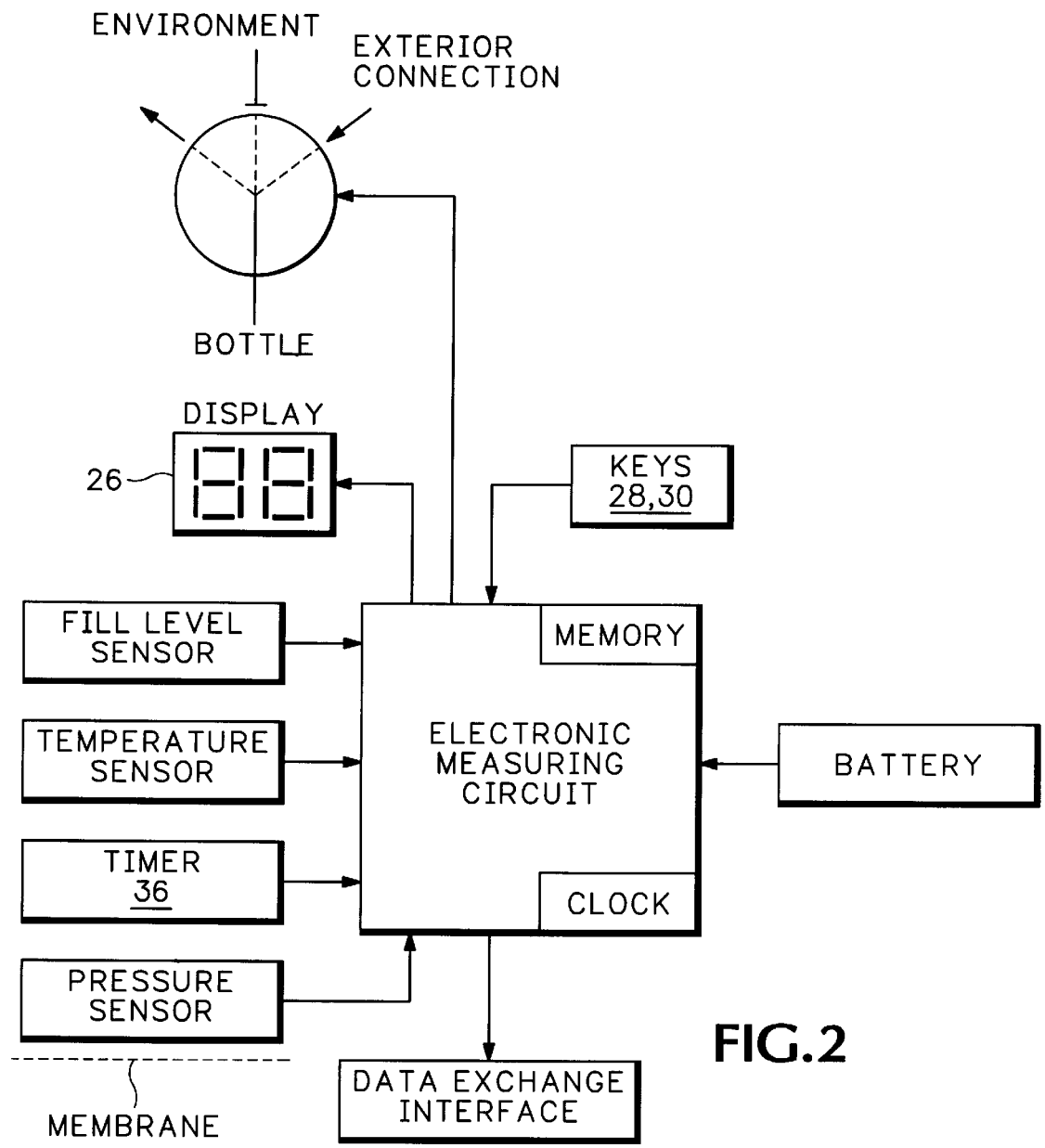
FIG. 2 is a block schematic diagram of the electronic measuring circuitry and associated components.

FIG. 1 shows an analytical device 10 comprising a bottle 12 and a measuring head 14 which screws onto the bottle 12. The measuring head 14 comprises a threaded part 16 which screws onto the bottle 12 and above which there is an enlarged part area 18 which has the shape of a sphere compressed along its vertical axis. The electrical or electronic components of the analytical device are integrated in this enlarged part 18. The enlarged part comprises two half shells 20, 22 which can be screwed together at a joint 24. A display 26 and two operating keys 28, 30 are provided in the area of the upper half shell 20. The outer contour of the display 26 extends flush with the outer contour of the upper half shell 20. The operating keys 28, 30 can easily extend above the outer surface of the upper half shell 20, however they are sealed liquid-tight, so that it is impossible for the device to become contaminated through the edges of the keys 28, 30. The display 26 is easily inclined upward, which makes it easier to read the readings shown on the display. In the example of the embodiment, a two-digit display is used. The two operating keys may be used individually or in combination to start and stop a measurement, to reset the device, or to display a reading. Similarly, the keys 28, 30 can be used to store certain values. If the device is intended for use in dark rooms, the display should be configured as an LED display. An automatic timer 36 (FIG. 2) (not shown) is provided in the device. It returns the electronic measuring circuitry to an idle state once the calculated value has appeared on the display for a specified time, for example between 10 seconds and 1 minute. In this idle state, current is applied only to the memory and, in some case, also to the measurement data acquisition circuit on the electronic measuring circuitry, so that the measuring head can be operated for a number of years with a single battery. A compartment for the battery or an accumulator is located in the area of the ends of the half shells 20, 22 facing one another, so that all that is required to replace the battery is to unscrew the half shells, replace the battery, and then screw the shells back together. Given the very low current consumption, which means that it is only necessary to change the battery once every two years, this device is very simple and easy to use.

Figure 3A:
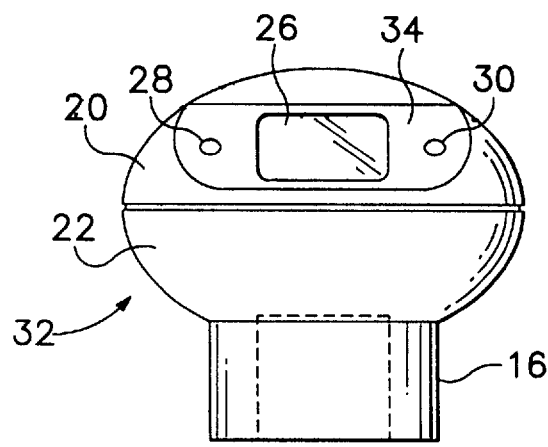
FIGS. 3A to 3C are views of an alternative embodiment of a measurement head to be used with the bottle shown in FIG. 1, FIG. 3A being a front elevation, FIG. 3B being a side elevation and FIG. 3C being a plan view.
Figure 3B:
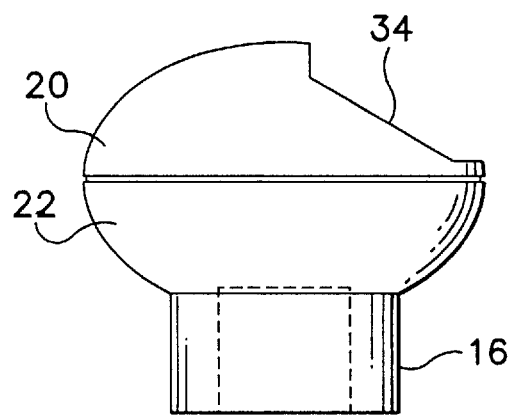
Figure 3C:
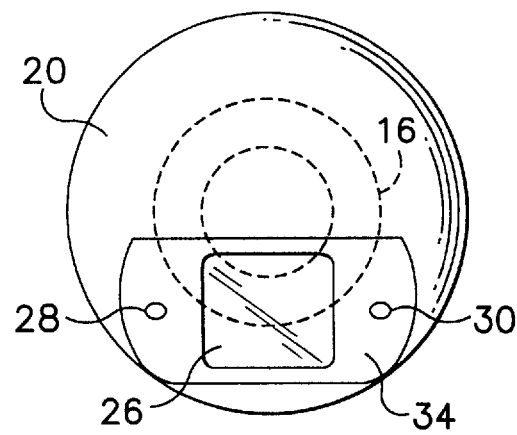

FIGS. 3A to 3C show various views of a measuring head 32, which is configured in a manner largely identical to the measuring head shown in FIG. 1. Identically or functionally equivalent parts are marked with the same reference numbers. Measuring head 32 differs from measuring head 14 in that it provides a flat area on the upper half shell 20 on which the keys 28, 30 and the display 26 are located. This flat area 34 is inclined at an angle of approximately 30° from the horizontal. Measuring head 32 has the advantage that the display can easily terminate close to the outer contour of the measuring head since the display can have a flat outer contour. Even though there are corners in the transition area from the flat area 34 to the outer contour of the upper half shell 20, this embodiment of the measuring head is more economical to produce due to the less expensive display or the less expensive display window protecting the display from the exterior. The cap 14, 32 is preferably manufactured from a plastic which offers as much chemical resistance as possible. It has extremely compact dimensions, which permits the bottles to be arranged close to one another, since the outer periphery of the measuring heads 14, 32 does not extend beyond the outer circumference of the corresponding bottles 12. The analytical device therefore is of an extremely space-saving and economical design, both with respect to its manufacture and to operation and maintenance.

I claim:

1. An analytical device for determining biological oxygen demand of waste water, comprising a container bounding an interior space to hold a sample of the waste water and a cap to seal the container in a gas-tight manner, wherein the cap contains:

an electrical pressure sensor in communication with the interior space of the container and operative to generate a pressure sensor output signal representative of pressure in said interior space, electronic measuring circuitry connected to receive the pressure sensor output signal and operative to calculate biological oxygen demand of the waste water in the container, the electronic measuring circuitry including a memory for storing reference and measured values, a user interface including keys to operate the electronic measuring circuitry and a display to display measured, calculated, or stored values, and a source of operating power for the electronic measuring circuitry.

2. An analytical device according to claim 1, wherein the cap contains a level sensor facing the interior space of the container for generating a level signal.

3. An analytical device according to claim 1, wherein the level sensor is connected to send the level signal to the electronic measuring circuitry and the electronic measuring circuitry is operative to use the level signal to calculate the biological oxygen demand.

4. An analytical device according to claim 1, wherein the cap contains an electrical temperature sensor which provides an output signal to the electronic measuring circuitry.

5. An analytical device according to claim 1, wherein the memory of the electronic measuring circuitry stores reference values.

6. An analytical device according to claim 1, wherein the memory of the electronic measuring circuitry stores a measured-value curve.

7. An analytical device according to claim 1, including a data exchange interface for exchanging data.

8. An analytical device according to claim 1, comprising an automatic timer and wherein the electronic measurement circuitry is programmed so that after completion of a measurement, the display shows the calculated value for a predetermined time and the electronic measuring circuitry then, in response to the automatic timer, switches to an idle state.

9. An analytical device according to claim 1, wherein the container is a bottle and the cap is a screw-on bottle cap.

10. An analytical device according to claim 9, wherein the bottle has a substantially cylindrical outer surface and the cap is configured in a rotationally symmetrical manner relative to a central axis of the bottle and has an outer surface of maximum radius relative to said central axis no greater than the radius of the outer surface of the bottle.

11. An analytical device according to claim 10, wherein the cap has a hemispherical or elliptical enlarged part in which the electrical components of the device are located.

12. An analytical device according to claim 11, wherein the source of operating power is a battery or accumulator and the enlarged part of the cap is composed of two half shells which can be connected to one another to form a tight seal, and a holder for the source of operating power is located in the area of the ends of the half shells which face one another.

13. An analytical device according to claim 1, wherein the display is an LCD or LED display having at least two columns.

14. An analytical device according to claim 1, wherein display extends to the an surface of the cap.

15. An analytical device according to claim 1, wherein the display is located in an upper surface of the cap and is inclined upward at an angle.

16. An analytical device according to claim 1, wherein the cap includes a valve which can be actuated electromagnetically by the electronic measuring circuitry in order to allow the interior of the container to communicate selectively either with the environment or with an exterior connection.

17. An analytical device according to claim 1, wherein the electronic measuring circuitry contains a clock or timer module.

18. An analytical device according to claim 1, wherein the pressure sensor is separated from the interior of the container by a gas-permeable water-repellent membrane.

* * * * *